United States Patent
Bogan et al.

(10) Patent No.: US 11,064,279 B2
(45) Date of Patent: Jul. 13, 2021

(54) HEADPHONE EARCUP INCLUDING SEAMLESS COVER

(71) Applicant: Microsoft Technology Licensing, LLC, Redmond, WA (US)

(72) Inventors: Kelly M. Bogan, Redmond, WA (US); Paul Ryan Sandoval, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 47 days.

(21) Appl. No.: 16/597,807

(22) Filed: Oct. 9, 2019

(65) Prior Publication Data

US 2021/0112326 A1 Apr. 15, 2021

(51) Int. Cl.
*H04R 1/10* (2006.01)
*A61F 11/14* (2006.01)

(52) U.S. Cl.
CPC ............ *H04R 1/1008* (2013.01); *A61F 11/14* (2013.01); *H04R 1/1083* (2013.01); *H04R 2201/105* (2013.01); *H04R 2460/15* (2013.01)

(58) Field of Classification Search
CPC .......................... H04R 1/1008; H04R 1/1083; H04R 2460/15; H04R 2201/105; A61F 11/14
See application file for complete search history.

(56) References Cited

U.S. PATENT DOCUMENTS

| | | | |
|---|---|---|---|
| 7,444,687 B2 * | 11/2008 | Sato | A61F 11/14 2/209 |
| 8,467,539 B2 * | 6/2013 | Sapiejewski | H04R 1/1008 381/71.6 |
| 9,438,980 B2 * | 9/2016 | Huang | H04R 1/1083 |
| 10,669,655 B2 * | 6/2020 | Hilton | D04B 1/102 |
| 2007/0036383 A1 | 2/2007 | Romero | |
| 2007/0044206 A1 | 3/2007 | Sato et al. | |
| 2019/0104353 A1 | 4/2019 | Ishikawa et al. | |

FOREIGN PATENT DOCUMENTS

| | | |
|---|---|---|
| CN | 104099717 A | 10/2004 |
| DE | 102006013831 A1 | 10/2007 |
| EP | 1867768 A1 | 12/2007 |
| EP | 1921889 A1 | 5/2008 |

(Continued)

OTHER PUBLICATIONS

"Replacement Earpads for Sony MDR-RF970R 960R RF925R RF860F RF985R, Headphones Ear Pads Cushion Headset Ear Cover with Memory Form", Retrieved from: https://www.amazon.com/Replacement-Earpads-MDR-RF970R-Headphones-Cushion/dp/B07D26L2MQ?ref_=fsclp_pl_dp_2, Aug. 13, 2019, 13 Pages.

(Continued)

*Primary Examiner* — Brian Ensey
(74) *Attorney, Agent, or Firm* — Wade IP Law PLLC

(57) ABSTRACT

A headphone device having an earcup that is configured to form a portion of an acoustic assembly of a headphone device. The earcup includes a seamless three-dimensional cover. The cover is formed from a continuous fabric of interlocking yarn. The cover can include portions having different performance characteristics, such as acoustic properties and/or comfort properties, that can be provided using different knit patterns and/or different fabric materials.

20 Claims, 10 Drawing Sheets

(56) References Cited

FOREIGN PATENT DOCUMENTS

| | | |
|---|---|---|
| JP | S48100114 A | 12/1973 |
| JP | S5133421 U | 3/1976 |
| JP | S59187281 U | 12/1984 |
| KR | 20110060706 A | 6/2011 |

OTHER PUBLICATIONS

"International Search Report and Written Opinion Issued in PCT Application No. PCT/US2020/048065", dated Nov. 17, 2020, 14 Pages.

* cited by examiner

HEADPHONE EARCUP INCLUDING SEAMLESS COVER

BACKGROUND

Headphone devices are often used to privately listen to an audio signal such as music, to conduct a conversation, or to block out noise. A user typically wears the headphone device so that acoustic assemblies, which may include speakers, included in the headphone device are positioned over the user's ears. With the advent of noise cancellation and the prevalence of gaming, the frequency and duration of use of headphone devices has increased. The increase in use has resulted in greater wear and tear; more demanding comfort, fit, and performance requirements; and a need to simplify the manufacture of the headphone devices.

SUMMARY

Various approaches are described herein for, among other things, providing an improved construction for an earcup that may be incorporated into a headphone device. For instance, an earcup includes a cover constructed of a seamless three-dimensional cover.

An example headphone earcup comprises a cover support, a coupling member, and a seamless three-dimensional knit cover. The cover support forms an earpad. The coupling member is configured to couple the earcup to an acoustic assembly housing. The seamless three-dimensional knit cover encloses the ear pad and is coupled to the coupling member. The knit cover defines an annular cavity for the ear pad, and is formed from a continuous contoured fabric of interlocking yarn. The knit cover comprises an outer portion, an inner portion, and an intermediate portion. The inner portion forms a side wall of a sound hole of the earcup. The intermediate portion extends between the outer portion and the inner portion and has an aperture that defines a perimeter of an opening of the sound hole. The intermediate portion has a different stiffness than at least one of the inner portion and the outer portion, and the different stiffness is due to at least one of a different knit pattern and a different fabric material.

A second example headphone earcup comprises a cover support, a coupling member, and a seamless three-dimensional knit cover. The cover support forms an ear pad. The coupling member is configured to couple the earcup to an acoustic assembly housing. The seamless three-dimensional knit cover is coupled to the coupling member. The knit cover defines an annular cavity and is coupled to the ear pad such that the cover support is disposed in the cavity. The knit cover is formed from a continuous contoured fabric of interlocking yarn. The knit cover comprises an outer portion, an inner portion, and an intermediate portion. The outer portion is configured to have a first acoustic transparency value. The inner portion forms a side wall of a sound hole and is configured to have a second acoustic transparency value. The intermediate portion is configured to have a third acoustic transparency value. The intermediate portion extends between the outer portion and the inner portion and defines a perimeter of the sound hole. The first acoustic transparency value is different than at least one of the second acoustic transparency value or the third acoustic transparency value.

An example method of making a headphone earcup comprises knitting a seamless three-dimensional knit cover, coupling a cover support to the knit cover, and coupling a coupling member to the knit cover. The knit cover defines an annular cavity. The knit cover is formed from a continuous contoured fabric of interlocking yarn and comprises an outer portion, an inner portion, and an intermediate portion. The inner portion forms a side wall of a sound hole. The intermediate portion defines an aperture that forms an opening of the sound hole and extending between the outer portion and the inner portion. The cover support is coupled to the knit cover so that the cover support is disposed in the annular cavity, and the cover support forms an ear pad. The coupling member is coupled to at least one of the outer portion or the inner portion.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Moreover, it is noted that the invention is not limited to the specific embodiments described in the Detailed Description and/or other sections of this document. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles involved and to enable a person skilled in the relevant art(s) to make and use the disclosed technologies.

Figure 1:
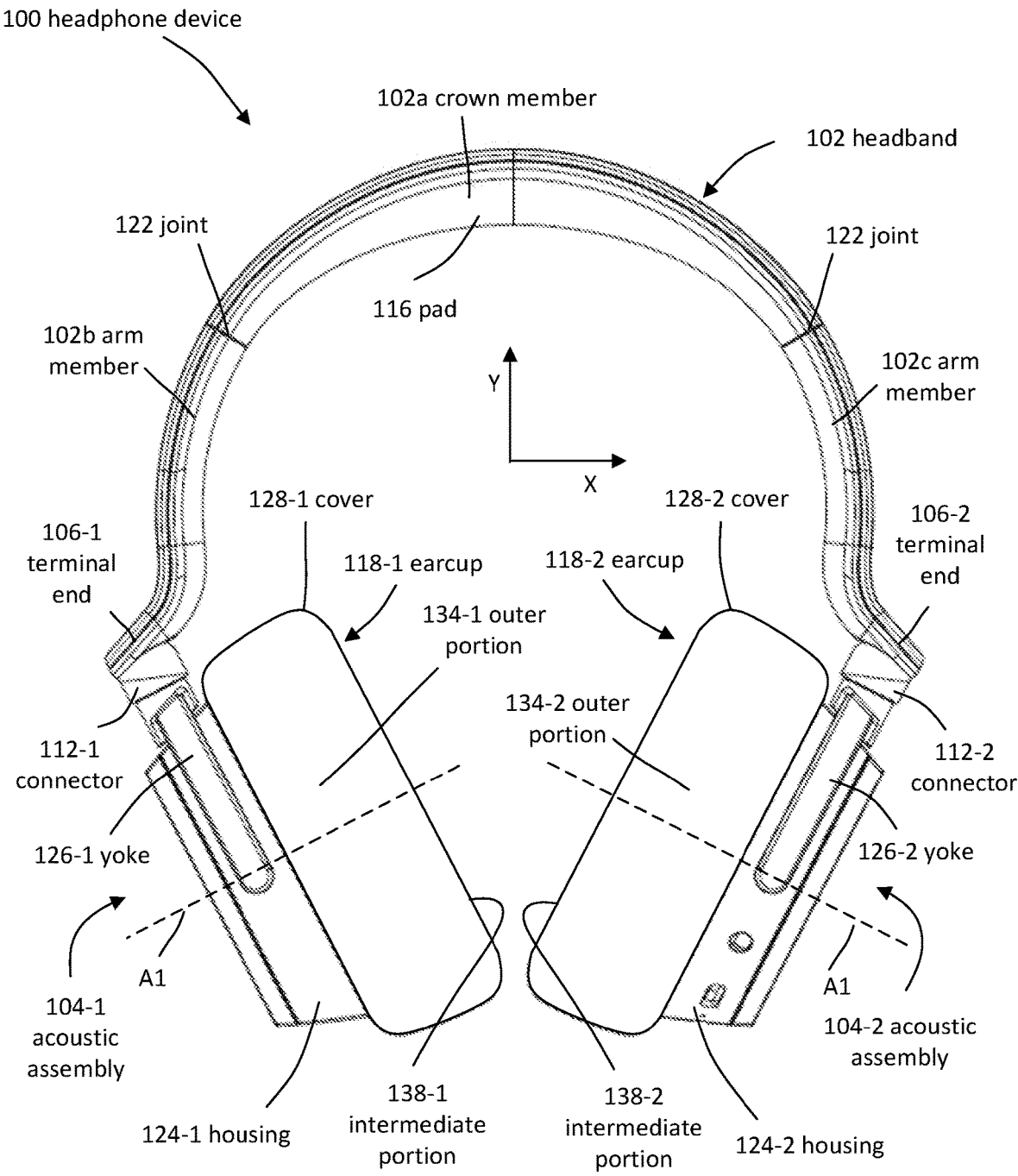
FIG. 1 is a side view of an example headphone device in accordance with at least one embodiment.

The features and advantages of the disclosed technologies will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The following detailed description refers to the accompanying drawings that illustrate example embodiments of the present invention. However, the scope of the present invention is not limited to these embodiments, but is instead defined by the appended claims. Thus, embodiments beyond those shown in the accompanying drawings, such as modified versions of the illustrated embodiments, may nevertheless be encompassed by the present invention.

References in the specification to "one embodiment," "an embodiment," "an example embodiment," or the like, indicate that the embodiment described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it is submitted that it is within the knowledge of one skilled in the relevant art(s) to implement such feature, structure, or characteristic in connection with other embodiments whether or not explicitly described.

II. Example Embodiments

Example embodiments described herein provide improvements over known earcups for headphone devices, such as audio headphones or hearing protection headphones. Example embodiments of the headphone device include an earcup construction that results in improved fit, comfort, performance, manufacturability, and serviceability of the earcup.

Earcups included in headphone devices are often manufactured using a multi-piece cover construction. Such a construction requires multiple pieces to be formed separately and coupled together to form the cover. The multiple pieces are coupled by forming seams and then the combined pieces are fit over a cover support that provides the shape of the earcup. The cover support must be formed to provide relief, such as in the form of a groove, to prevent the seams from creating a discontinuous and/or undesired outer contour of the earcup. As a result, the production of the cover requires multiple unnecessary and time-consuming steps that can be avoided using a seamless three-dimensional cover in accordance with at least one embodiment.

Additionally, the multi-piece construction of the cover allows for a common failure mode of earcups, i.e., the delamination of the seams. That failure mode can be avoided by employing a seamless three-dimensional cover in accordance with at least one embodiment. In particular, the seams are oftentimes formed by welding, adhering and/or stitching multiple cover pieces together. With repeated use, and the associated application of heat and moisture, the seams can delaminate. The removal of the seams in the seamless three-dimensional cover avoids the failure mode and provides the ability to tune portions of the earcup cover for desired fit, comfort, and/or performance.

Figure 2:
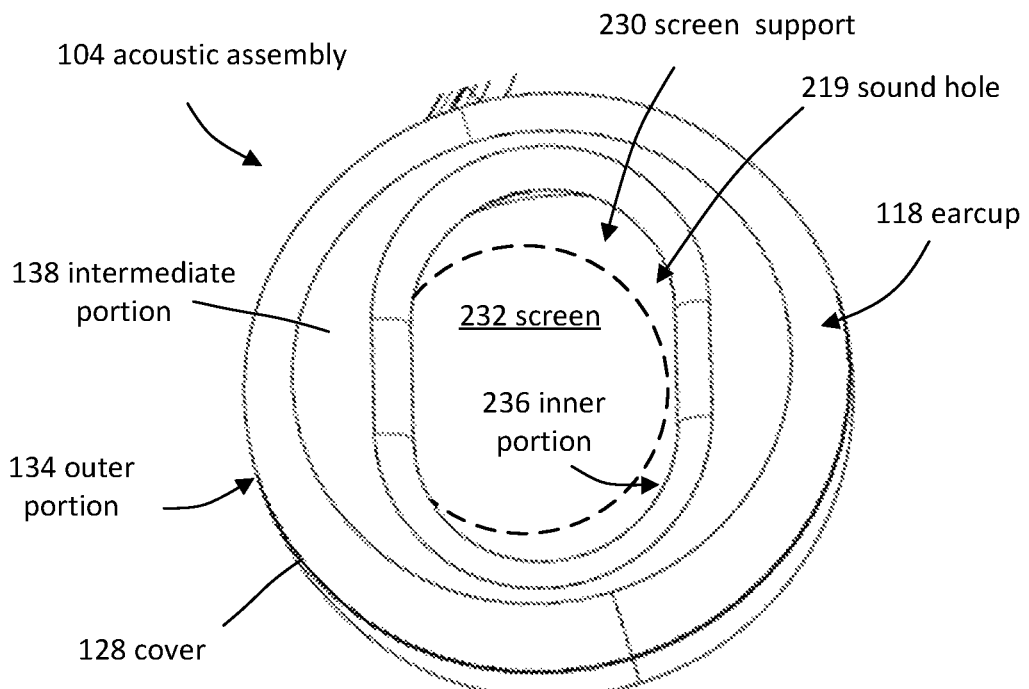
FIG. 2 is a side view of a portion of an example headphone device in accordance with at least one embodiment.
Figure 3:
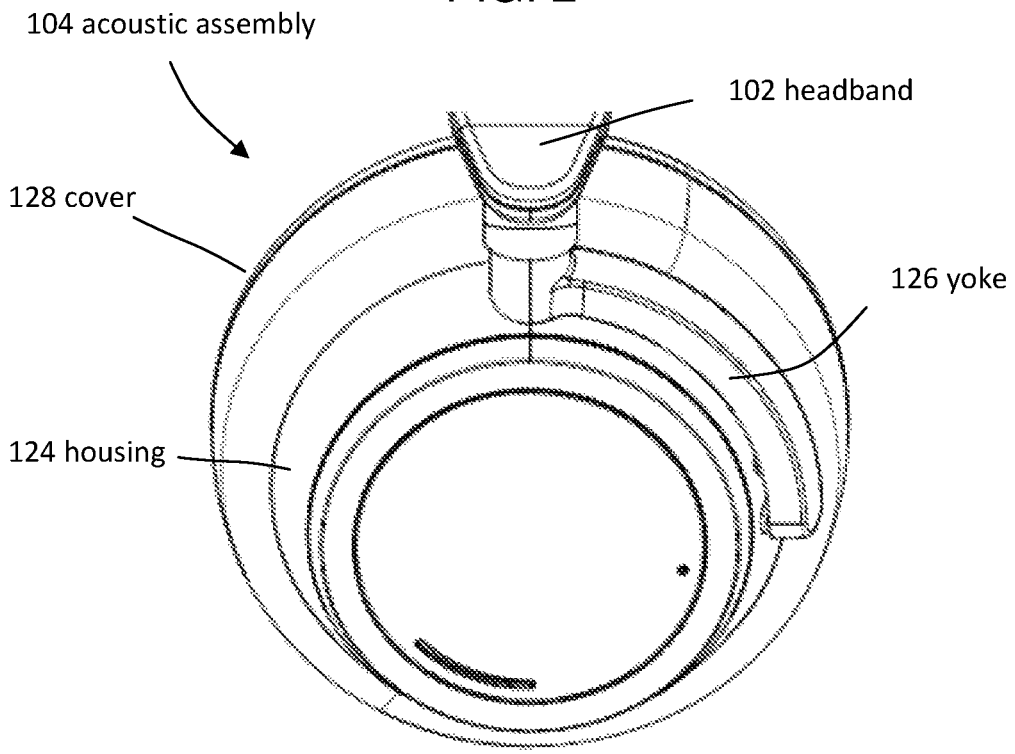
FIG. 3 is a side view of a portion of an example headphone device in accordance with at least one embodiment.

FIGS. 1-3 illustrate at least one embodiment of a headphone device 100 that may include an earcup in accordance with at least one embodiment. The headphone device 100 comprises a headband 102, and acoustic assemblies 104 (e.g., acoustic assemblies 104-1 and 104-2) coupled to terminal ends 106 (e.g., terminal ends 106-1 and 106-2) of the headband 102. The headband 102 is configured to space the acoustic assemblies 104 from each other. The headband 102 can be flexible to allow for adjustment in the spacing and orientation between the acoustic assemblies 104 to adjust the fit on a user.

Connectors 112 (e.g., connectors 112-1 and 112-2) movably couple the headband 102 to the acoustic assemblies 104. Each of the connectors 112 is configured to allow the respective acoustic assembly 104 to be oriented to provide an optimal ergonomic fit over a user's ear. Each of the acoustic assemblies 104 can be coupled to the headband 102 so that the respective acoustic assembly can be rotated relative to the headband 102 over any span. In at least one embodiment, the acoustic assembly can rotate relative to the headband 102 over a span of about 90°. In some embodiments, the acoustic assembly can rotate relative to the headband 102 in a span up to 180°. In some embodiments, the acoustic assembly can rotate relative to the headband 102 over a span that is greater than 180°.

The terminal ends 106 of the headband 102 are spaced so that the acoustic assemblies 104 are held in a spaced relationship from each other by the headband 102. The spaced relationship between the acoustic assemblies 104 places the acoustic assemblies in a predefined location and orientation so that earcups can be positioned over a user's ears. In that position, the acoustic assemblies 104 are configured to direct an audible signal toward the user's ears (e.g., using audio headphones) and/or to prevent high-intensity sound from reaching the user's ears (e.g., using hearing protection headphones, or audio headphones with noise cancellation).

The headband 102 comprises an elongate body that is interposed between the acoustic assemblies 104. In at least one embodiment, the headband 102 is configured to rest on the top of a user's head, such as on the rearward portion of the user's frontal bone, on the forward portion of the user's parietal bone, and/or at a location where the front bone meets the parietal bone. It should be appreciated that the headband can be configured to rest over any portion of the user's head when the headphone device is worn by the user.

The headband 102 is configured to provide a desired fit of the headphone device 100 on the user. The shape and materials used in the construction of the headband 102 can be selected to provide the desired fit of the headphone device 100. In at least one embodiment, the shape of the headband 102 is arcuate and sized to correspond to the contour of a user's head. Additionally, the headband 102 can comprise a pad 116 that is oriented on an inner portion of the headband 102 so that the pad 116 is positioned to abut the user's head. In at least one embodiment, the pad 116 is removeable so that it can be easily cleaned and/or replaced by the user.

The headband 102 can also include at least a portion that is flexible. The flexible portion of the headband 102 forms a spring between the acoustic assemblies 104. The head band 102 can be configured to provide a spring force that is selected so that the acoustic assemblies 104 exert a predefined force on the sides of a user's head. In at least one embodiment, the spring force is selected so that the predefined force results in earcups 118 (e.g., earcups 118-1 and 118-2) of the acoustic assemblies 104 providing seals against the user's head that reduces leakage of ambient noise past the earcups and into the user's ears. Additionally, the spring force can be selected to provide friction between the user's head and the acoustic assemblies 104 to reduce relative motion between the user's head and the headphone device 100. In at least one embodiment, the entire headband 102 is constructed to be flexible.

The headband 102 can also be configured to provide a desired fit by including a length adjustment feature. As an example, the headband 102 can comprise one or more telescoping joints 122 that permit a user to alter the length of the headband 102. In at least one embodiment, the headband 102 comprises a discontinuous elongate body that is constructed from a plurality of components, such as a crown member 102a, a first arm member 102b, and a second arm member 102c. The headband 102 can further comprise an extension member that extends across each discontinuity in the elongate body. The extension member can be slidably coupled across the discontinuity between the headband components to at least one of the adjacent portions of the elongate body thereby forming the telescoping joint 122. Additionally, the extension member and/or the elongate body can comprise détente features to provide defined length settings and can provide audible and/or tactile feedback to a user while the user alters the length of the headband 102.

Additionally, the headband 102 can form a housing for electronics included in the headphone device 100. For example, the headband 102 can define a cavity that houses circuitry. The cavity can also provide a conduit for wiring included in the construction of the headphone device 100.

In at least one embodiment, each acoustic assembly 104 includes the earcup 118, a housing 124 (e.g., housings 124-1 and 124-2), and a yoke 126 (e.g., yokes 126-1 and 126-2). The earcup 118 is shaped and sized to provide a desired fit over, or on, a user's ear. The earcup 118 can define a sound hole 219 and can be constructed to define performance characteristics, such as acoustic properties (e.g., audio transparency) and comfort properties (e.g., cushioning, stiffness, or surface texture). The earcup 118 can include a cover 128 (e.g., covers 128-1 and 128-2) that at least partially encloses a cover support (e.g., an earpad), a coupling member, a screen support 230, and a screen 232.

The cover 128 is constructed as a seamless three-dimensional body. In some embodiments, the cover 128 is knit. In some embodiments, the cover 128 is formed from a continuous contoured fabric of interlocking fibers or yarn. The three-dimensional shape can provide a contour that defines the overall annular shape of the cover 128. In some embodiments, the three-dimensional shape results in the cover defining an annular cavity and the cover support can be disposed in the annular cavity.

As used herein "annular" is not limited to circular shapes for either the exterior shape or the interior shape and is intended to describe a generally ring shape that may or may not include circular shapes. An annular body may have an exterior shape that is different from an interior shape. Additionally, the centroids of the interior shape and the exterior shape need not coincide so that the annulus can have a width that varies at locations around the circumference. For example, the outer perimeter can provide an exterior shape that may be a circle, an oval, a polygon, or irregular. Regardless of the exterior shape, the interior shape can be a circle, an oval, a polygon, or irregular. In the example embodiment shown in FIG. 2, the earcup 118 is annular and includes a circular exterior shape and an ovular interior shape.

The cover 128 can include an outer portion 134 (e.g., outer portions 134-1 and 134-2), an inner portion 236, and an intermediate portion 138 (e.g., intermediate portions 138-1 and 138-2). The outer portion 134 forms the radially outermost surface of the cover 128 of the earcup 118 relative to a central axis A1 of the acoustic assembly 104. The inner portion 236 forms an inner side wall of the cover 128 of the earcup 118 and is disposed radially inward from the outer portion 134 relative to the central axis A1 so that it forms the side wall of the sound hole 219.

The intermediate portion 138 extends between the outer portion 134 and the inner portion 236 and generally provides a contact, or ear-abutting, surface of the cover 128. The intermediate portion 138 can include an aperture that defines a perimeter of an opening of the sound hole 219 closest to a user's ear. The intermediate portion 138 can have a stiffness that is different from a stiffness of the outer portion 134 and/or a stiffness of the inner portion 236 so that it provides cushioning to a user. As will be described in greater detail, the difference in stiffness can be due to at least one of a different knit pattern or a different fabric material in the region of the intermediate portion 138.

Regions of the continuous fabric forming the outer portion, the inner portion, and the intermediate portion in each of the example cover embodiments described herein can be configured to provide different acoustic transparency values. For example, the outer portion 134 can be configured to have a first acoustic transparency value, the inner portion 236 can be configured to have a second acoustic transparency value, and the intermediate portion 138 can be configured to have a third acoustic transparency value. In at least one embodiment, the first acoustic transparency value is different than at least one of the second acoustic transparency value or the third acoustic transparency value. In at least one embodiment, the first acoustic transparency value is lower than at least one of the second acoustic transparency value and the third acoustic transparency value.

The cover support can form an ear pad that provides cushioning to a user. The cover support can be shaped to complement the shape of the annular cavity defined by the cover 128. In some embodiments, the cover 128 is constructed so that it is rigid enough to maintain the desired shape and flexibility without being supported by a cover support. In some embodiments, the cover support can be optional or can be configured to occupy only a portion of the annular cavity of the cover.

The coupling member provides an interface between the housing 124 and the earcup 118. In some embodiments, the coupling member is configured to provide a removable coupling between the housing 124 and the earcup 118 so that the earcup 118 can be removed and/or replaced. The coupling member and/or the housing 124 can include coupling features that can be configured to retain the earcup 118 with the housing 124. The coupling features can be configured to provide an interlocking by relative rotation between the earcup 118 and the housing 124. Alternatively, snap fits, press fits, interference fits, or any other interlocking mechanism that prevents the earcup 118 from separating from the housing 124 during use can be employed.

The screen support 230 provides a support structure for the screen 232. The screen support 230 can provide a flange for coupling the screen 232 to the other components of the earcup 118. The screen support 230 can be a separate component, or it can be integrated into another component, such as the cover 128. The screen support 230 can be rigid, or semi-rigid, so that the screen support 230 provides a structure that supports and orients the screen 232. The screen support 230 can have a stiffness that is greater than a stiffness of the screen 232. In at least one embodiment, the screen support 230 has a stiffness that is greater than a stiffness of the intermediate portion 138 of the cover 128.

The screen support 230 can be an annular member so that it forms an aperture that allows an audible signal to pass through the screen support 230 and to be directed toward the user's ear. The screen support 230 can be contoured or planar.

The screen 232 can be provided in the acoustic assembly 104 to extend across a portion of the sound hole 219 that is defined by the earcup 118. In some embodiments, the screen 232 is configured to alter the acoustic characteristics of the earcup 118. In some embodiments, the screen is configured to provide a comfort property, such as by providing ventilation. The screen 232 can also, or alternatively, be configured to protect components housed in the housing 124 when the earcup 118 is attached. For example, the screen 232 can be configured to prevent the ingress of moisture and/or debris into the housing 124.

The housing 124 provides a structure for supporting and protecting components of the acoustic assembly 104 such as audio components. For example, the audio components can include an audio output device, such as a digital or analog speaker, and electronics that support the audio output device. The components can also include controls and supporting control electronics for controlling volume, connectivity, etc.

The yoke 126 is an optional component that can be used to couple the housing 124 to the connector 112 to provide improved fit for a user by allowing additional adjustment of the position of the acoustic assembly 104 relative to the headband 102. For example, the connector 112 can rotatably couple the yoke 126 to the headband 102 to permit relative rotation about a first axis of rotation between the yoke 126 and the headband 102. The yoke 126 can also be rotatably coupled to the housing 124 to permit relative rotation about a second axis of rotation between the yoke 126 and the housing 124 that is different than the first axis of rotation to provide additional adjustment for a user to fit the headphone device 100. The yoke 126 can have many different configurations that provide a linkage between the connector 112 and the housing 124 and can be omitted if desired.

The acoustic assemblies 104 can have a variety of configurations. The acoustic assemblies can be configured to provide an audible signal and/or to limit the exposure of the user's ear to noise. In at least one embodiment, the headphone device 100 is audio headphones and each acoustic assembly is configured as a speaker assembly. The speaker assembly may, or may not, also incorporate noise-cancellation technology. In at least one embodiment, the headphone device 100 is hearing protection headphones and each acoustic assembly can be configured as a sound earmuff assembly. The sound earmuff assembly may, or may not, also incorporate noise-cancellation technology.

Figure 4:
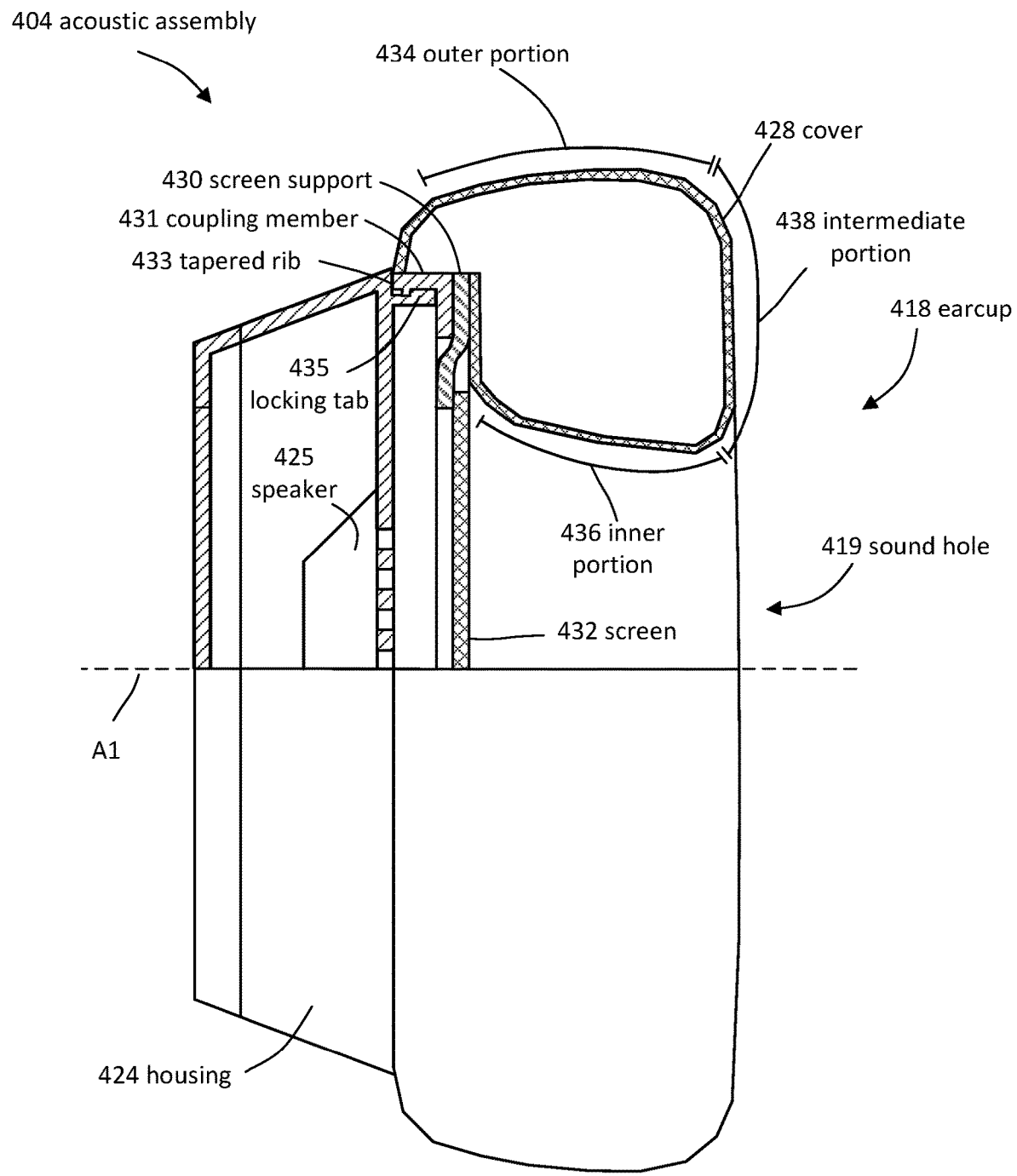
FIG. 4 is a partial cross-sectional view of an acoustic assembly of an example headphone device in accordance with at least one embodiment.
Figure 5:
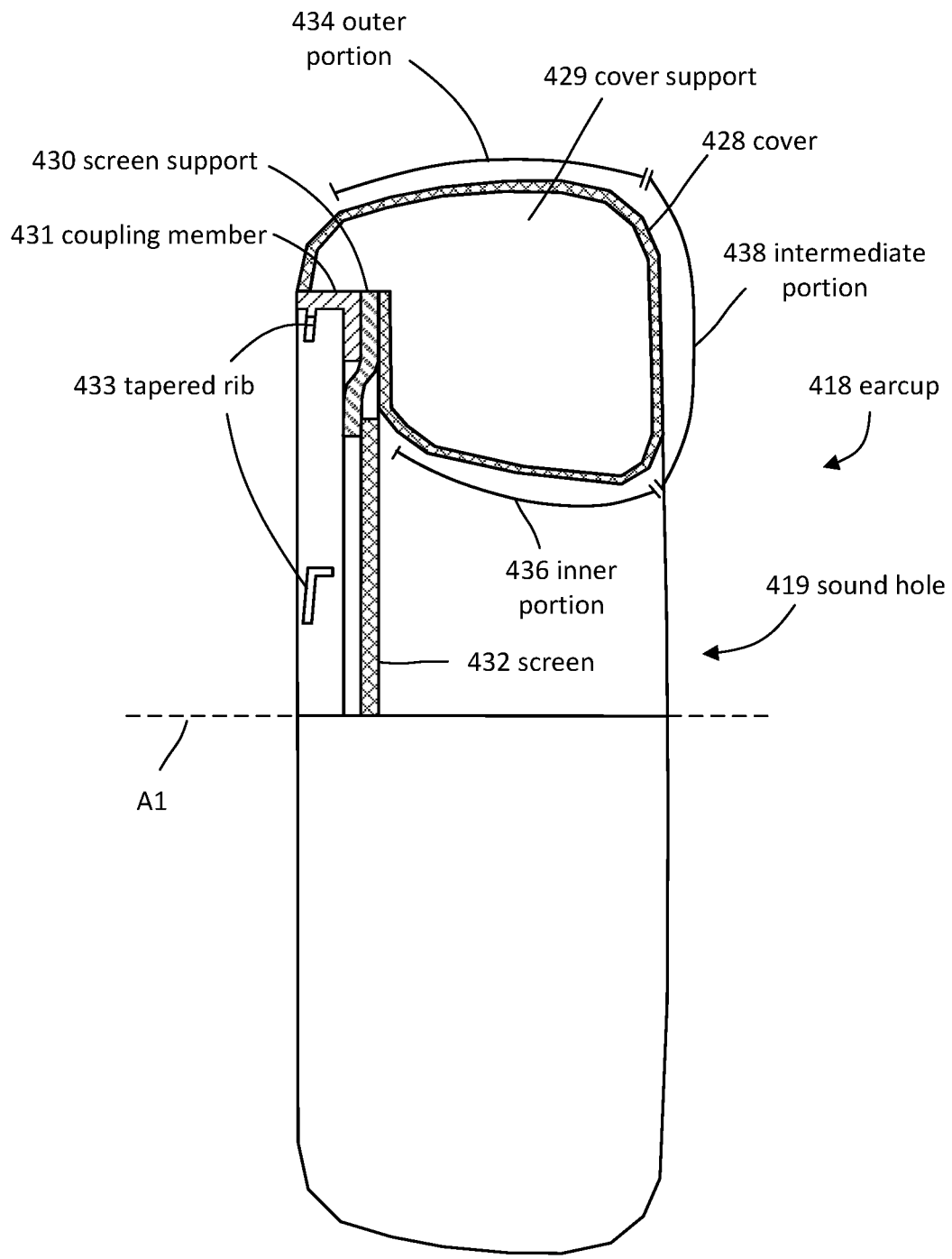
FIG. 5 is a partial cross-sectional view of an earcup of the acoustic assembly of FIG. 4 in accordance with at least one embodiment.

FIG. 4 illustrates an example acoustic assembly 404 that includes an earcup 418 (also shown in FIG. 5). In some embodiments, the acoustic assembly 404 is the acoustic assembly 104. The acoustic assembly 404 includes an earcup 418, and a housing 424. The earcup 418 is shaped and sized to provide a desired fit over, or on, a user's ear. The earcup 418 is generally annular and defines a sound hole 419 that extends in the direction of a central axis A1 of the acoustic assembly 404. The earcup 418 can be constructed to define performance characteristics, such as acoustic properties (e.g., audio transparency) and comfort properties (e.g., stiffness, or surface texture).

The earcup 418 can be assembled from a cover 428 that at least partially encloses a cover support 429 (e.g., an earpad), a coupling member 431, a screen support 430, and a screen 432. The cover 428 is constructed as a seamless three-dimensional body. In some embodiments, the cover 428 is knit. In some embodiments, the cover 428 is formed from a continuous contoured fabric of interlocking fibers or yarn. The three-dimensional shape can provide a contour that defines an overall annular shape of the cover 428. In example embodiments, the three-dimensional shape results in the cover defining an annular cavity and the cover support 429 can be disposed in the annular cavity. In the illustrated embodiment, the cover 428 is initially constructed separate from each of the coupling member 431, the screen support 430, and the screen 432, but it should be appreciated that any, or all, of those components can be integrally formed as part of the cover, as will be described in greater detail with regard to additional embodiments.

The cover 428 can include an outer portion 434, an inner portion 436, and an intermediate portion 438. The region of the fabric forming each of the outer portion 434, the inner portion 436, and the intermediate portion 438 can be tailored to provide desired performance characteristics for each of the portions. For example, even though the cover 428 is constructed as a seamless three-dimensional cover formed from a continuous fabric, different regions of the fabric can be constructed to provide different performance characteristics, such as by including different knit patterns and/or different materials.

The outer portion 434 forms the radially outermost surface of the cover 428 of the earcup 418 relative to a central axis A1 of the acoustic assembly 404. The outer portion 434 forms the portion of the cover 428 that is most exposed to environmental conditions, such as ambient noise, moisture and debris, when the acoustic assembly 404 is worn by a user. In at least one embodiment, a region of the continuous fabric forming the outer portion 434 includes a knit pattern having a stitch density that is high enough to reduce the acoustic transparency of the outer portion 434. In at least one other example embodiment, the region of the continuous fabric forming the outer portion 434 is finished to provide moisture resistance and/or resistance to becoming soiled.

The inner portion 436 forms the radially innermost surface of the cover 428 of the earcup 418 relative to the central axis A1 of the acoustic assembly 404. The inner portion 436 forms a side wall of the sound hole 419 and is most exposed to a user's inner ear when the acoustic assembly 404 is worn by a user. In an example embodiment, a region of the continuous fabric forming the inner portion 436 includes a knit pattern having a stitch density that is low enough to allow ventilation of heat and moisture from the sound hole 419 and away from the user's ear. In at least one other example embodiment, the region of the continuous fabric forming the inner portion 436 is finished to provide moisture resistance.

The intermediate portion 438 extends between the outer portion 434 and the inner portion 436 and forms a surface of the cover 428 that is spaced from the housing 424 in a direction parallel to the central axis A1 of the acoustic assembly 404. The intermediate portion 438 provides an ear-abutting surface that contacts a user's head when the acoustic assembly 404 is worn by a user. In some embodiments, a region of the continuous fabric forming the intermediate portion 438 includes a knit pattern having a stitch density that is low enough to allow ventilation of heat and moisture away from the user. In some embodiments, the region of the continuous fabric forming the intermediate portion 438 is finished to provide moisture resistance, soiling resistance, and/or to provide desired softness or suppleness. In some embodiments, the region of the continuous fabric forming the intermediate portion 438 includes thermoset and/or thermoplastic filaments that can be used to provide a desired flexibility of the intermediate portion 438 so that the cover 428 is constructed to provide cushioning to the user during use.

The cover support 429 can be formed as an ear pad that provides a cushioning structure that fills at least a portion of the annular cavity defined by the cover 428. In at least one embodiment, the cover support 429 entirely fills the annular cavity defined by the cover 428. In at least one embodiment, the cover support 429 fills only a portion of the annular cavity defined by the cover 428. In at least one embodiment, the cover 428 is constructed to have properties, such as stiffness and cushioning, allowing the cover support to be optional. The outer surface of the cover support 429 can be shaped to complement the inner shape of the annular cavity defined by the cover 428. The seamless construction of the continuous fabric of the cover 428 permits the construction of the cover support 429 to be simplified. In particular, because there are no seams between components forming the cover, there is no need to include relief slots or grooves in the cover support 429 that would otherwise receive the seams and allow for a smoother outer contour of the cover.

The coupling member 431 provides an interface between the housing 424 and the earcup 418. In the illustrated embodiment, the coupling member 431 and the housing 424 include coupling features that are configured to retain the earcup 418 with the housing 424. For example, the coupling features can include features that interlock when the parts are rotated relative to each other. For example, the coupling member 431 can include tapered ribs 433 that extends radially inward, and the housing 424 can include a tapered slot and/or a locking tab 435 that slidably abuts the tapered rib 433 so that relative rotation between the coupling member 431 and the housing 424 draw the coupling member 431 and the housing 424 together.

The screen support 430 provides a support structure for the screen 432. The screen support 430 can provide a flange for coupling the screen 432 to the other components of the earcup 418. The screen support 430 can be rigid, or semi-rigid, so that the screen support 430 provides a structure that orients the screen 432. For example, the screen support 430 can have a stiffness greater than a stiffness of the screen 432, and/or greater than a stiffness of the intermediate portion 438. The screen support 430 can be an annular member so that it forms an aperture that allows an audible signal to pass through the screen support 430 and to be directed toward the user's ear. The screen support 430 can be contoured or planar.

The screen 432 can be provided in the acoustic assembly 404 to extend across a portion of the sound hole 419 that is defined by the earcup 418. The screen 432 can be disposed at any location in the sound hole 419, such as at an end of the sound hole 419 closest to the housing 424 and the coupling member 431. In some embodiments, the screen 432 is configured to alter the acoustic characteristics of the earcup 418. In some embodiments, the screen 432 is configured to provide ventilation so that moisture and/or heat can escape from the sound hole 419 and be directed away from the user's ear. The screen 432 can also, or alternatively, be configured to protect components housed in the housing 424 when the earcup 418 is attached. For example, the screen 432 can be configured to prevent the ingress of moisture and/or debris into the housing 424.

The housing 424 provides a structure for supporting and protecting components of the acoustic assembly 404 such as audio components. For example, the audio components can include an audio output device, such as a digital or analog speaker 425, and electronics that support the audio output device. The components can also include controls and supporting control electronics for controlling volume, connectivity, etc.

Figure 6:
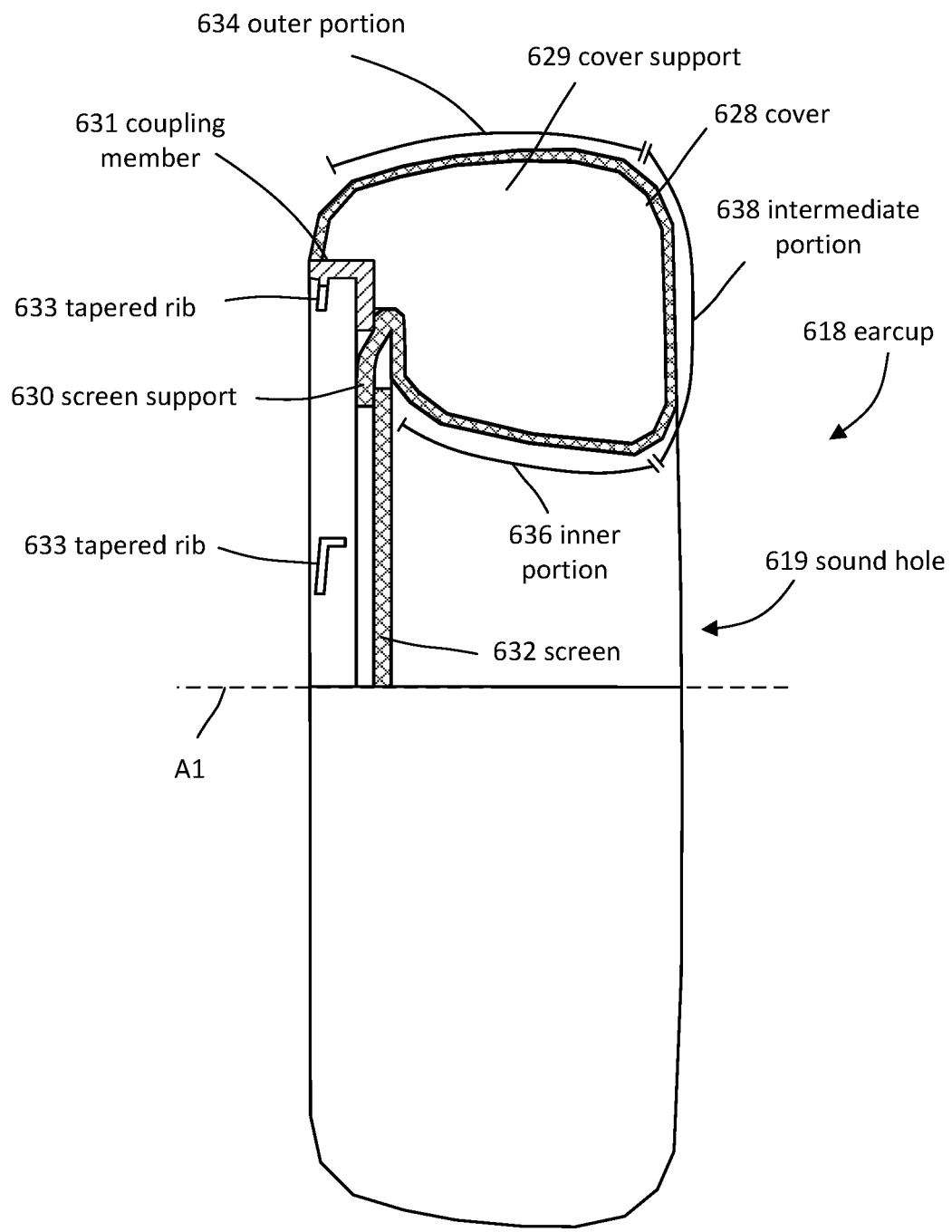
FIG. 6 is a partial cross-sectional view of an earcup of an acoustic assembly in accordance with at least one embodiment.

Referring to FIG. 6, another example embodiment of an earcup that can be incorporated into an acoustic assembly, such as by replacing earcup 418 of acoustic assembly 404, will be described. The earcup 618 includes a cover 628 that at least partially encloses a cover support 629 (e.g., an earpad), a coupling member 631, a screen support 630, and a screen 632. Similar to other example embodiments, the cover 628 is constructed as a seamless three-dimensional body. In some embodiments, the cover 628 is knit. In some embodiments, the cover 628 is formed from a continuous contoured fabric of interlocking fiber or yarn. The three-dimensional shape can provide a contour that defines an overall annular shape of the cover 628. In some embodiments, the three-dimensional shape results in the cover defining an annular cavity and the cover support 629 can be disposed in the annular cavity. In the illustrated embodiment, the cover 628 is constructed so that the screen support 630 is integrated into the continuous construction, but separate from each of the coupling member 631, and the screen 632.

The cover 628 includes an outer portion 634, an inner portion 636, an intermediate portion 638, and a screen support portion 630. The region of the fabric forming each of the outer portion 634, the inner portion 636, the intermediate portion 638, and the screen support portion 630 can be tailored to provide desired performance characteristics for each of the portions. For example, even though the cover 628 is constructed as a seamless three-dimensional cover formed from a continuous fabric, different regions of the fabric can be constructed to provide different performance characteristics, such as by including different knit patterns and/or different materials.

The outer portion 634 forms the radially outermost surface of the cover 628 of the earcup 618 relative to a central axis A1 of an acoustic assembly. The outer portion 634 forms the portion of the cover 628 that is most exposed to environmental conditions, such as ambient noise, moisture and debris, when the acoustic assembly is worn by a user. In at least one embodiment, a region of the continuous fabric forming the outer portion 634 includes a knit pattern having a stitch density that is high enough to reduce the acoustic transparency of the outer portion 634. In some embodiments, the region of the continuous fabric forming the outer portion 634 is finished to provide moisture resistance and/or resistance to becoming soiled.

The inner portion 636 forms the radially innermost surface of the cover 628 of the earcup 618 relative to the central axis A1 of the acoustic assembly. The inner portion 636 forms a side wall of a sound hole 619 and is most exposed to a user's inner ear when the acoustic assembly is worn by a user. In at least one embodiment, a region of the continuous fabric forming the inner portion 636 includes a knit pattern having a stitch density that is low enough to allow ventilation of heat and moisture from the sound hole 619 and away from the user's ear. In some embodiments, the region of the continuous fabric forming the inner portion 636 is finished to provide moisture resistance.

The intermediate portion 638 extends between the outer portion 634 and the inner portion 636 and forms a surface of the cover 628 that is spaced from a housing of the acoustic assembly in a direction parallel to the central axis A1. The intermediate portion 638 provides an ear-abutting surface that contacts a user's head when the acoustic assembly is worn by a user. In at least one example embodiment, a region of the continuous fabric forming the intermediate portion 638 includes a knit pattern having a stitch density that is low enough to allow ventilation of heat and moisture away from the user. In some embodiments, the region of the continuous fabric forming the intermediate portion 638 is finished to provide moisture resistance, soiling resistance, and/or to provide desired softness or suppleness. In some embodiments, the region of the continuous fabric forming the intermediate portion 638 includes filaments that can be shaped using heat and used to provide a desired flexibility of the intermediate portion 638 so that the cover 628 is constructed to provide cushioning to the user during use.

The screen support 630 of earcup 618 is integrated into the cover 628. For example, the screen support 630 is formed as part of the seamless three-dimensional cover and formed by a region of the continuous contoured fabric of the cover 628. The screen support 630 provides a support for the screen 632. The screen support 630 can provide a flange for coupling the screen 632 to the other components of the earcup 618. The screen support 630 can be rigid, or semi-rigid, so that the screen support 630 provides a structure that orients the screen 632. For example, the screen support 630 can have a stiffness greater than a stiffness of the screen 632, and/or greater than a stiffness of the intermediate portion 638. The screen support 630 can be an annular member so that it forms an aperture that allows an audible signal to pass through the screen support 630 and to be directed toward the user's ear.

The cover support 629 can be formed as an ear pad that provides a cushioning structure that fills at least a portion of the annular cavity defined by the cover 628. In some embodiments, the cover support 629 entirely fills the annular cavity defined by the cover 628. In some embodiments, the cover support 629 fills only a portion of the annular cavity defined by the cover 628. In some embodiments, the cover 628 is constructed to have properties, such as stiffness and cushioning, allowing the cover support to be optional. The outer surface of the cover support 629 can be shaped to complement the inner shape of the annular cavity defined by the cover 628.

The coupling member 631 provides an interface between a housing of the acoustic assembly and the earcup 618. The coupling member 631 includes coupling features that are configured to interact with the housing to retain the earcup 618 with the housing. For example, the coupling member 631 can include tapered ribs 633 that are configured to interact with and engage coupling features on the housing, such as locking tabs, to couple the parts.

The screen 632 can be provided in the acoustic assembly to extend across a portion of the sound hole 619 that is defined by the earcup 618. The screen 632 can be disposed at any location in the sound hole 619, such as at an end of the sound hole 619 closest to the coupling member 631. In some embodiments, the screen 632 is configured to alter the acoustic characteristics of the earcup 618. In some embodiments, the screen 632 is configured to provide ventilation so that moisture and/or heat can escape from sound hole 619 so that moves away from the user's ear. The screen 632 can also, or alternatively, be configured to protect components housed in a housing included in the acoustic assembly. For example, the screen 632 can be configured to prevent the ingress of moisture and/or debris into the housing.

Figure 7:
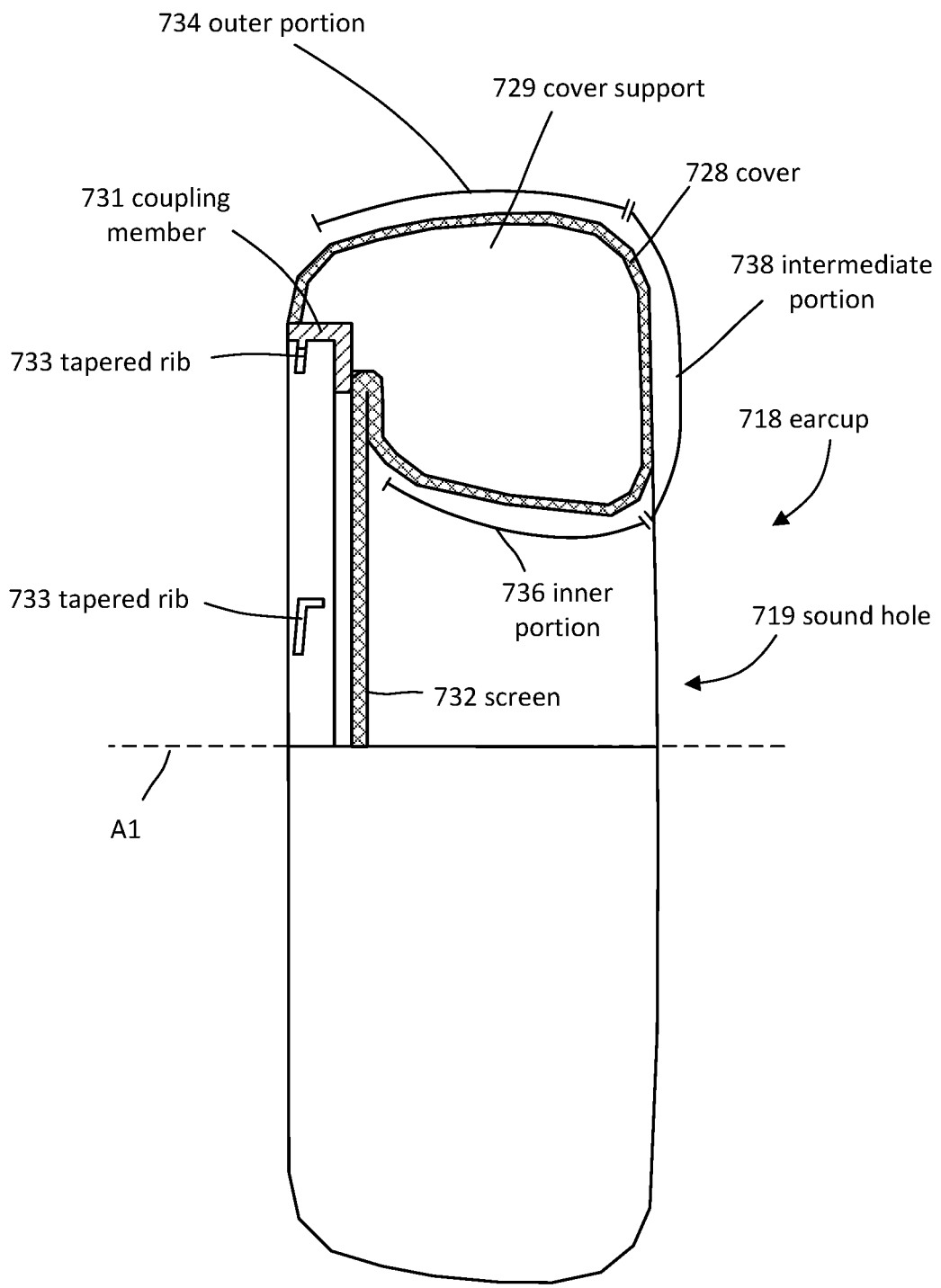
FIG. 7 is a partial cross-sectional view of an earcup of an acoustic assembly in accordance with at least one embodiment.

Referring to FIG. 7, another example embodiment of an earcup that can be incorporated into an acoustic assembly, such as by replacing earcup 418 of acoustic assembly 404, will be described. The earcup 718 includes a cover 728 that at least partially encloses a cover support 729 (e.g., an ear pad), a coupling member 731, and a screen 732. Similar to other example embodiments, the cover 728 is constructed as a seamless three-dimensional body. In some embodiments, the cover 728 is knit. In some embodiments, the cover 728 is formed from a continuous contoured fabric of interlocking fibers or yarn. The three-dimensional shape can provide a contour that defines an overall annular shape of the cover 728. In example embodiments, the three-dimensional shape results in the cover defining an annular cavity and the cover support 729 can be disposed in the annular cavity. In the illustrated embodiment, the cover 728 is constructed so that the screen 732 is integrated into the continuous construction, and the earcup 718 does not include a screen support.

The cover 728 includes an outer portion 734, an inner portion 736, an intermediate portion 738, and a screen portion 732. The region of the fabric forming each of the outer portion 734, the inner portion 736, the intermediate portion 738, and the screen portion 732 can be tailored to provide desired performance characteristics for each of the portions. For example, even though the cover 728 is constructed as a seamless three-dimensional cover formed from a continuous fabric, different regions of the fabric can be constructed to provide different performance characteristics, such as by including different knit patterns and/or different materials.

The outer portion 734 forms the radially outermost surface of the cover 728 of the earcup 718 relative to a central axis A1 of an acoustic assembly. The outer portion 734 forms the portion of the cover 728 that is most exposed to environmental conditions, such as ambient noise, moisture and debris, when the acoustic assembly is worn by a user. In some embodiments, a region of the continuous fabric forming the outer portion 734 includes a knit pattern having a stitch density that is high enough to reduce the acoustic transparency of the outer portion 734. In some embodiments, the region of the continuous fabric forming the outer portion 734 is finished to provide moisture resistance and/or resistance to becoming soiled.

The inner portion 736 forms the radially innermost surface of the cover 728 of the earcup 718 relative to the central axis A1 of the acoustic assembly. The inner portion 736 forms a side wall of a sound hole 719 and is most exposed to a user's inner ear when the acoustic assembly is worn by a user. In some embodiments, a region of the continuous fabric forming the inner portion 736 includes a knit pattern having a stitch density that is low enough to allow ventilation of heat and moisture from the sound hole 719 and away from the user's ear. In some embodiments, the region of the continuous fabric forming the inner portion 736 is finished to provide moisture resistance.

The intermediate portion 738 extends between the outer portion 734 and the inner portion 736 and forms a surface of the cover 728 that is spaced from a housing of the acoustic assembly in a direction parallel to the central axis A1. The intermediate portion 738 provides an ear-abutting surface that contacts a user's head when the acoustic assembly is worn by a user. In some embodiments, a region of the continuous fabric forming the intermediate portion 738 includes a knit pattern having a stitch density that is low enough to allow ventilation of heat and moisture away from the user. In some embodiments, the region of the continuous fabric forming the intermediate portion 738 is finished to provide moisture resistance, soiling resistance, and/or to provide desired softness or suppleness. In some embodiments, the region of the continuous fabric forming the intermediate portion 738 includes filaments that can be shaped using heat to provide a desired flexibility of the intermediate portion 738 so that the cover 728 is constructed to provide cushioning to the user during use.

The screen 732 of earcup 718 is integrated into the cover 728. The screen 732 can be provided in the acoustic assembly to extend across a portion of a sound hole 719 that is defined by the earcup 718. The screen 732 extends from an edge of the inner portion 736 and across the sound hole 719. As illustrated, the screen 732 is disposed at an end of the sound hole 719 closest to the coupling member 731. In some embodiments, the screen 732 is configured to alter the acoustic characteristics of the earcup 718. In some embodiments, the screen 732 is configured to provide ventilation so that moisture and/or heat can escape from sound hole 719 so that moves away from the user's ear. The screen 732 can also, or alternatively, be configured to protect components housed in a housing included in the acoustic assembly. For example, the screen 732 can be configured to prevent the ingress of moisture and/or debris into the housing.

The cover support 729 can be formed as an ear pad that provides a cushioning structure that fills at least a portion of the annular cavity defined by the cover 728. In some embodiments, the cover support 729 entirely fills the annular cavity defined by the cover 728. In some embodiments, the cover support 729 fills only a portion of the annular cavity defined by the cover 728. In some embodiments, the cover 628 is constructed to have properties, such as stiffness and cushioning, allowing the cover support to be optional. The outer surface of the cover support 729 can be shaped to complement the inner shape of the annular cavity defined by the cover 728.

The coupling member 731 provides an interface between a housing of the acoustic assembly and the earcup 718. The coupling member 731 includes coupling features that are configured to interact with the housing to retain the earcup 718 with the housing. For example, the coupling member 731 can include tapered ribs 733 that are configured to interact with coupling features, such as locking tabs, on the housing of the acoustic assembly to couple the parts.

Figure 8:
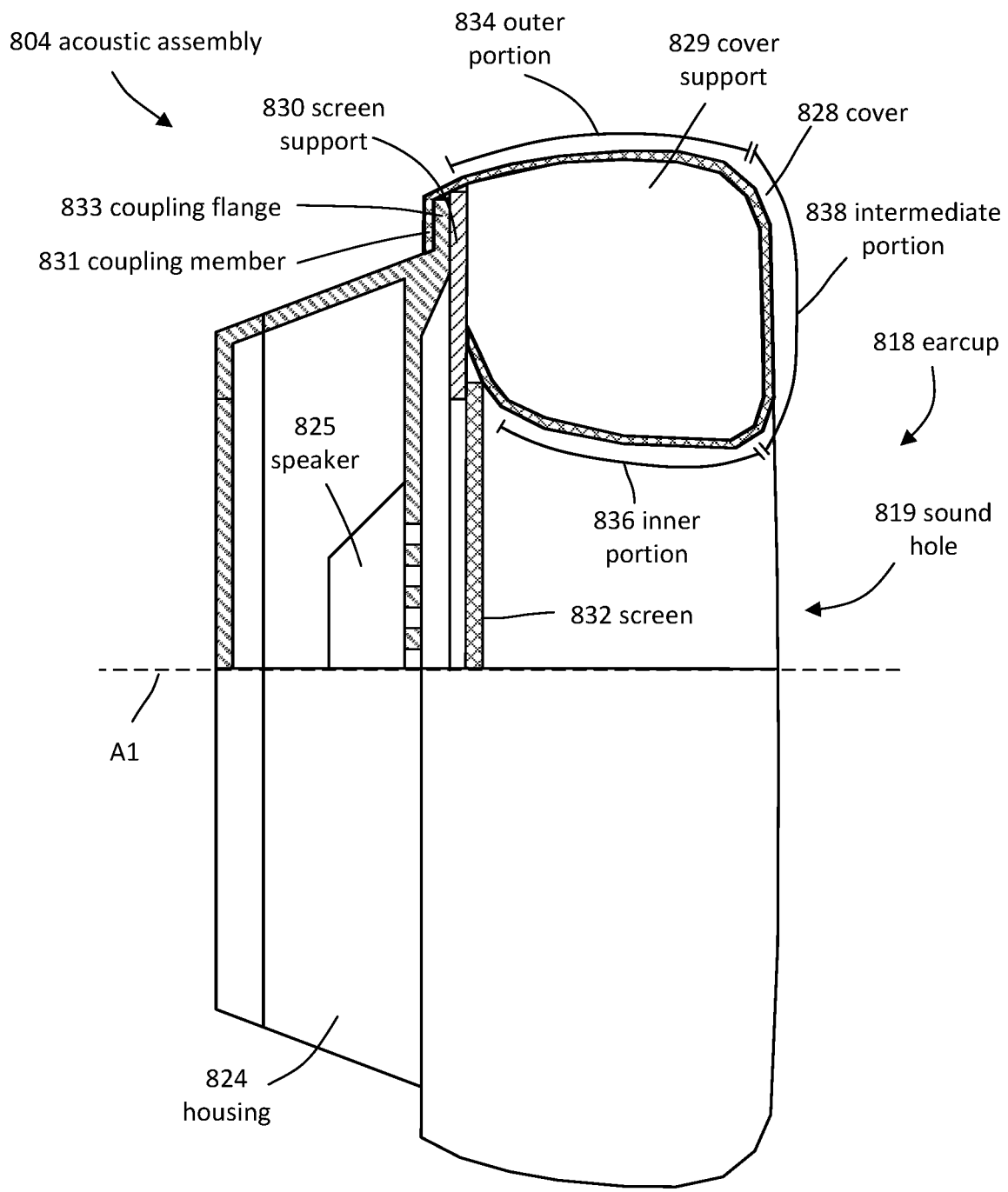
FIG. 8 is a partial cross-sectional view of an acoustic assembly of an example headphone device in accordance with at least one embodiment.
Figure 9:
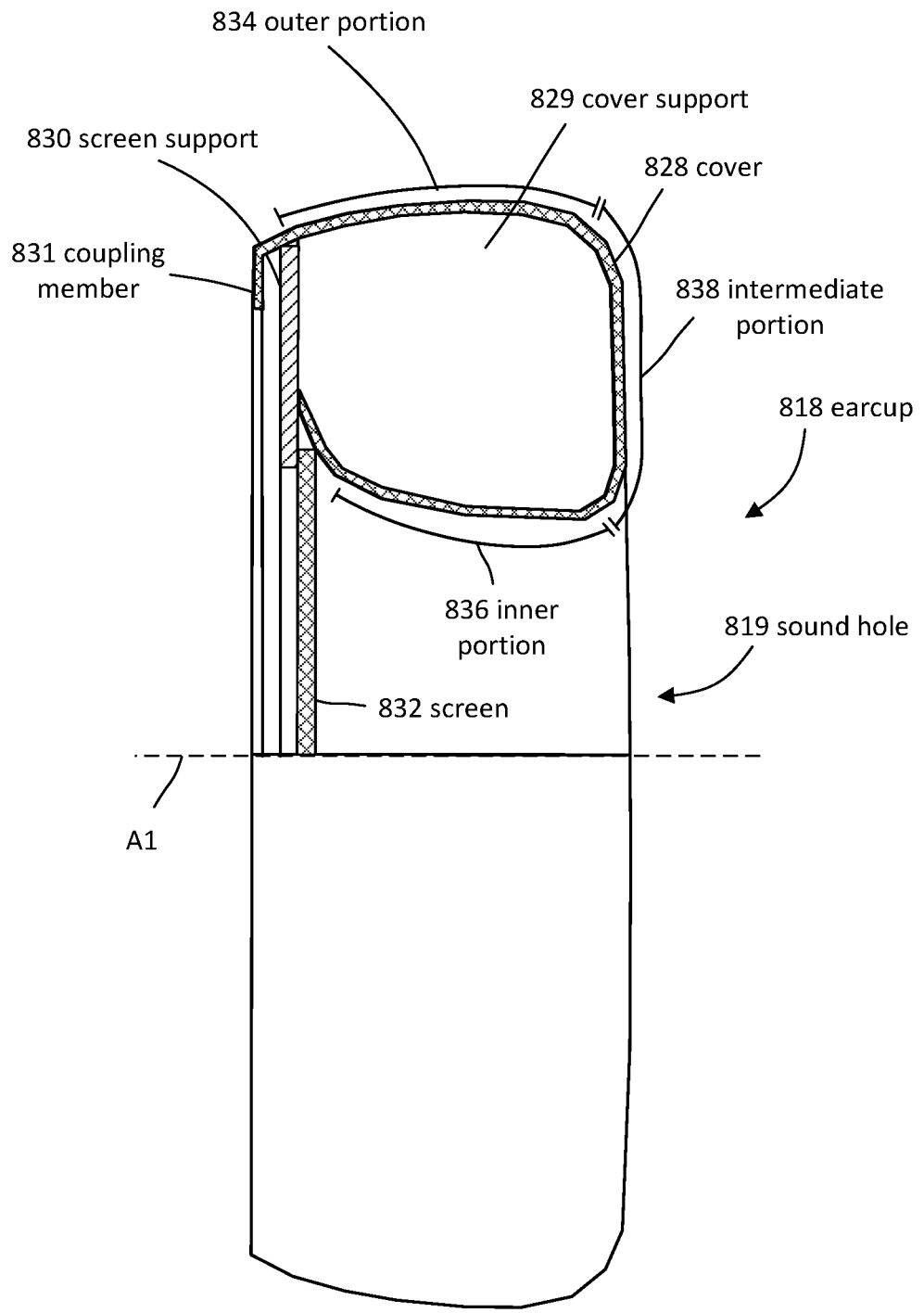
FIG. 9 is a partial cross-sectional view of an earcup of the acoustic assembly of FIG. 8 in accordance with at least one embodiment.

FIG. 8 illustrates an example acoustic assembly 804 that includes an earcup 818 (also shown in FIG. 9). In some embodiments, the acoustic assembly 804 is the acoustic assembly 104. The acoustic assembly 804 includes an earcup 818, and a housing 824. The earcup 818 is shaped and sized to provide a desired fit over, or on, a user's ear. The earcup 818 is generally annular and defines a sound hole 819 that extends in the direction of a central axis A1 of the acoustic assembly 804. The earcup 818 can be constructed to define performance characteristics, such as acoustic properties (e.g., audio transparency) and comfort properties (e.g., stiffness, or surface texture).

The earcup 818 can be assembled from a cover 828 that at least partially encloses a cover support 829 (e.g., an ear pad), a coupling member 831, a screen support 830, and a screen 832. The cover 828 is constructed as a seamless three-dimensional body. In some embodiments, the cover 828 is knit. In some embodiments, the cover is formed from a continuous contoured fabric of interlocking yarn. The three-dimensional shape can provide a contour that defines an overall annular shape of the cover 828. In some embodiments, the three-dimensional shape results in the cover defining an annular cavity and the cover support 829 can be disposed in the annular cavity. Additionally, in the illustrated embodiment, the cover 828 is constructed so that the coupling member 831 is integrated into the continuous construction of the cover 828.

The cover 828 can include an outer portion 834, an inner portion 836, an intermediate portion 838, and the coupling member 831. The region of the fabric forming each of the outer portion 834, the inner portion 836, the intermediate portion 838, and the coupling member 831 can be tailored to provide desired performance characteristics for each of the portions. For example, even though the cover 828 is constructed as a seamless three-dimensional cover formed from a continuous fabric, different regions of the fabric can be constructed to provide different performance characteristics, such as by including different knit patterns and/or different materials.

The outer portion 834 forms the radially outermost surface of the cover 828 of the earcup 818 relative to a central axis A1 of the acoustic assembly 804. The outer portion 834 forms the portion of the cover 828 that is most exposed to environmental conditions, such as ambient noise, moisture and debris, when the acoustic assembly 804 is worn by a user. In some embodiments, a region of the continuous fabric forming the outer portion 834 includes a knit pattern having a stitch density that is high enough to reduce the acoustic transparency of the outer portion 834. In some embodiments, the region of the continuous fabric forming the outer portion 834 is finished to provide moisture resistance and/or resistance to becoming soiled.

The inner portion 836 forms the radially innermost surface of the cover 828 of the earcup 818 relative to the central axis A1 of the acoustic assembly 804. The inner portion 836 forms a side wall of the sound hole 819 and is most exposed to a user's inner ear when the acoustic assembly 804 is worn by a user. In some embodiments, a region of the continuous fabric forming the inner portion 836 includes a knit pattern having a stitch density that is low enough to allow ventilation of heat and moisture from the sound hole 819 and away from the user's ear. In some embodiments, the region of the continuous fabric forming the inner portion 836 is finished to provide moisture resistance.

The intermediate portion 838 forms a surface of the cover 828 that is spaced from the housing 824 in a direction parallel to the central axis A1 of the acoustic assembly 804. The intermediate portion 838 provides an ear-abutting surface that contacts a user's head when the acoustic assembly 804 is worn by a user. In some embodiments, a region of the continuous fabric forming the intermediate portion 838 includes a knit pattern having a stitch density that is low enough to allow ventilation of heat and moisture away from the user. In some embodiments, the region of the continuous fabric forming the intermediate portion 838 is finished to provide moisture resistance, soiling resistance, and/or to provide desired softness or suppleness. In some embodiments, the region of the continuous fabric forming the intermediate portion 838 includes filaments that can be shaped using heat and used to provide a desired flexibility of the intermediate portion 838 so that the cover 828 is constructed to provide cushioning to the user during use.

The coupling member 831 provides an interface between the housing 824 and the earcup 818. In the illustrated embodiment, the coupling member 831 is a flange that is formed integrally as a portion of the cover 828. The housing 824 includes a coupling feature, such as a coupling flange 833, that is received and retained in an undercut defined by the coupling member 831. The coupling member 831 is configured to be flexible enough to stretch over the coupling flange 833 and to retain the coupling flange 833. The flexibility of the coupling member 831 can be provided by selecting the knit pattern and materials included in that region of the continuous fabric of the cover 828.

The screen support 830 provides a support for the screen 832. The screen support 830 can provide a flange for coupling the screen 832 to the other components of the earcup 818. The screen support 830 can be rigid, or semi-rigid, so that the screen support 830 provides a structure that orients the screen 832. For example, the screen support 830 can have a stiffness greater than a stiffness of the screen 832, and/or greater than a stiffness of the intermediate portion 838. The screen support 830 can be an annular member so that it forms an aperture that allows an audible signal to pass through the screen support 830 and to be directed toward the user's ear. As illustrated, the screen support 830 is planar.

The screen 832 can be provided in the acoustic assembly 804 to extend across a portion of the sound hole 819 that is defined by the earcup 818. The screen 832 can be disposed at any location in the sound hole 819, such as at an end of the sound hole 819 closest to the housing 824 and the coupling member 831. In some embodiments, the screen 832 is configured to alter the acoustic characteristics of the earcup 818. In some embodiments, the screen 832 is configured to provide ventilation so that moisture and/or heat can escape from sound hole 819 so that moves away from the user's ear. The screen 832 can also, or alternatively, be configured to protect components housed in the housing 824 when the earcup 818 is attached. For example, the screen 832 can be configured to prevent the ingress of moisture and/or debris into the housing 484.

Similar to previously described example embodiments, the housing 824 provides a structure for supporting and protecting components of the acoustic assembly 804 such as audio components. For example, the audio components can include an audio output device, such as a speaker 825 that can be a digital or analog speaker, and electronics that support the audio output device. The components can also include controls and supporting control electronics for controlling volume, connectivity, etc.

The cover support 829 can be formed as an ear pad that provides a cushioning structure that fills at least a portion of the annular cavity defined by the cover 828. In some embodiments, the cover support 829 entirely fills the annular cavity defined by the cover 828. In some embodiments, the cover support 829 fills only a portion of the annular cavity defined by the cover 828. In some embodiments, the cover 828 is constructed to have properties, such as stiffness and cushioning, allowing the cover support to be optional. The outer surface of the cover support 829 can be shaped to complement the inner shape of the annular cavity defined by the cover 828.

In each of the example embodiments, the cover can be constructed using synthetic yarn, such as by knitting the cover using a weft-knitting machine so that the knit cover has the three-dimensional shape knit into the structure. In some embodiments, a near final three-dimensional shape of the cover is knit into the structure and a secondary process, such as applying heat, is used to shape the knit cover into the final three-dimensional shape. The secondary process can be performed applying heat while using a shaped cover support, a mold, or another shaping jig. In some embodiments, the synthetic yarn can be extruded. The synthetic yarn can be constructed from a plurality of filaments. In some embodiments, the synthetic yarn is constructed from at least one filament that is formed of a material that can be shaped and set to retain the shape using heat. For example, the yarn can include thermoset and/or thermoplastic polymers. The yarn can be constructed from materials such as multifilament polyester or nylon. The yarn could be made as an extruded polymer, cellulose, or regenerated cellulose fiber. The yarn structure may be single, twisted, texturized or core-spun. To achieve a range of finished textile weights, a yarn size may have a range from 40 dtex to 300 dtex. To achieve a range of surface textures and structures multiple types of yarns may be used in the same knitted piece.

The cover can also be constructed so that the continuous contoured fabric includes portions having different interlocking constructions, such as knit patterns, to provide different performance characteristics. In some embodiments utilizing weft knits, the patterns can include single knits, double knits, and/or specialized knits that are combined to form the continuous fabric. Examples of single knit patterns include single jersey, and lacoste. Examples of double knit patterns include rib, purl, interlock, cable fabric, bird's eye, cardigans, milano ribs, and pointelle. Examples of specialized knit patterns include intarsia, jacquard jerseys, knitted terry, knitted velour, sliver knit, fleece, and French terry.

In some embodiments, portions include an interlocking construction that provides larger openings where greater audio transparency and/or more ventilation is desired. These openings are achieved by using a missed or a tuck stitch in the knit pattern. In some embodiments, portions include an interlocking construction that provides smaller openings where lower audio transparency and/or less ventilation is desired. Attributes such as mass, density, thickness, compression, porosity and perforation, air permeability and flow resistivity, tortuosity, and surface features can be selected to provide different performance characteristics, such as audio transparency and/or ventilation.

Still further, portions can be finished using different techniques to provide different textures, shapes, appearances, sound absorption, sound transparency, moisture resistance, soiling resistance, etc. For example, finishing processes that can be applied to the cover materials include scouring, heat-setting, post-setting, stiffening, and filling. Additionally, one or more finishes can be applied to the cover materials such as hydrophobic, anti-pilling, anti-static, nonslip, sizing and anti-microbial finishes. The finishing techniques can be mechanical and/or chemical finishing techniques.

In each of the example embodiments, the cover support can be constructed from a flexible material or structure. For example, the cover support can be constructed from a foam material, such as memory foam. In some embodiments, the cover support can completely fill the annular cavity defined by the cover, or partially fill the annular cavity. The cover support can be formed from a foam material having a density in a range of between about 1.0 lb/ft$^3$ and about 3.0 lb/ft$^3$. In some embodiments, the cover support is formed from a foam material having a density in a range of between about 1.5 lb/ft$^3$ and about 2.5 lb/ft$^3$. The cover support can be formed from foam materials including viscoelastic polyurethane foam or low-resilience polyurethane foam. In alternative examples, the cover support can be formed as a flexible framework or lattice structure. In some embodiments, the cover support is a tubular member that fills the annular cavity defined by the cover and provides the desired structure and cushioning.

Figure 10:
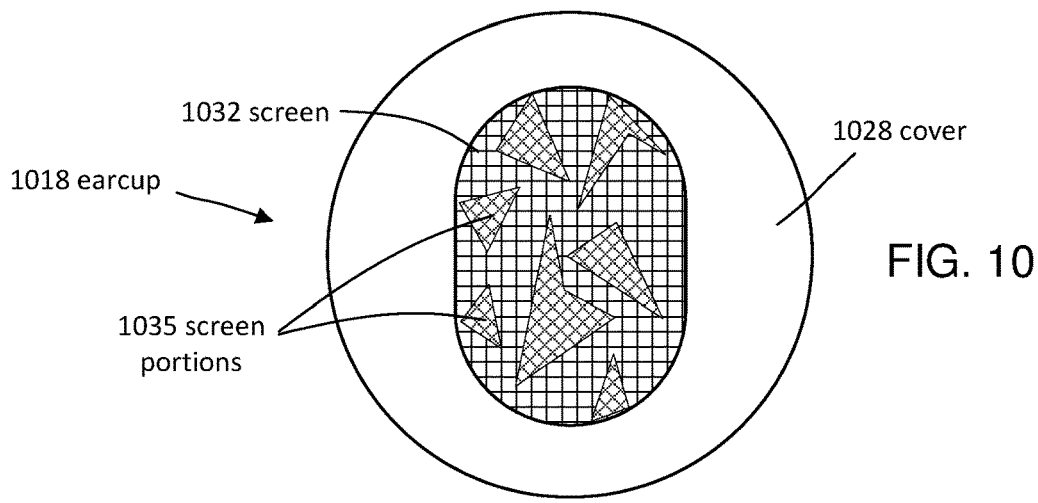
FIGS. 10-12 are side views of example earcups in accordance with various embodiments.

The screen of the earcup can be configured to have portions having different performance characteristics, such as acoustic properties and/or comfort properties, and/or indicia. Referring to FIG. 10, an earcup 1018 includes a cover 1028 and a screen 1032. The cover 1028 can at least partially encompasses a cover support, such as an ear pad. The screen 1032 can include screen portions 1035 having different performance characteristics, such as audio transparency, and/or ventilation. The screen portions 1035 can be configured to have geometric shapes, such as screen portions 1035 which are illustrated as having generally polygonal shapes. The screen portions 1035 can be sized, positioned, and/or configured to have a desired audio transparency to alter the overall performance characteristics of the screen 1032. The screen portions 1035 and remainder of screen 1032 can have different knit patterns, and/or materials to provide desired performance characteristics.

Figure 11:
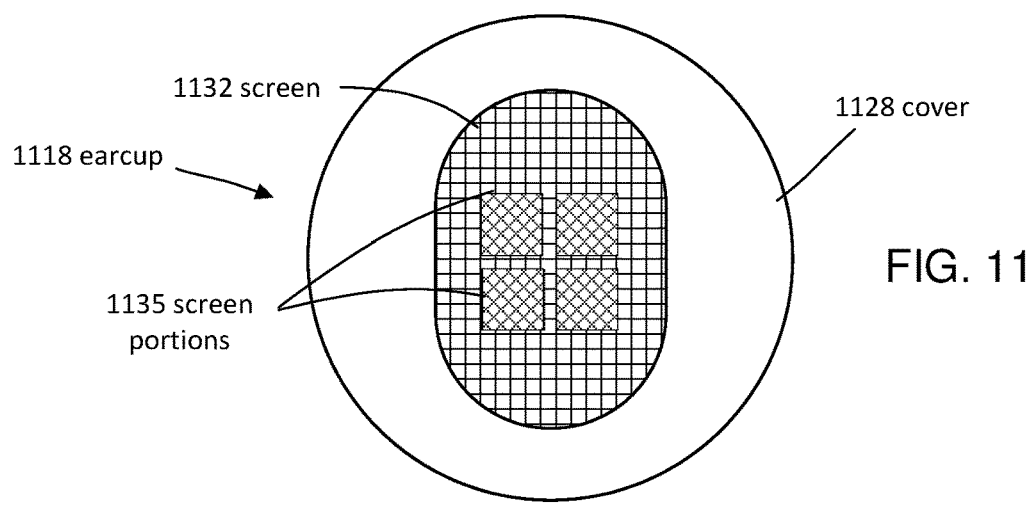

Referring to FIG. 11, in another example embodiment an earcup 1118 includes a cover 1128 and a screen 1132. The cover 1128 can at least partially encompasses a cover support, such as an ear pad. The screen 1132 can include portions having different performance characteristics, such as audio transparency, and/or ventilation. In the illustrated embodiment, screen portions 1135 of the screen 1132 are configured to form a grid pattern. The screen portions 1035 can be sized, positioned, and/or configured to have a desired audio transparency to alter the overall performance characteristics of the screen 1132. The screen portions 1135 and remainder of screen 1132 can have different knit patterns, and/or materials to provide desired performance characteristics.

Figure 12:
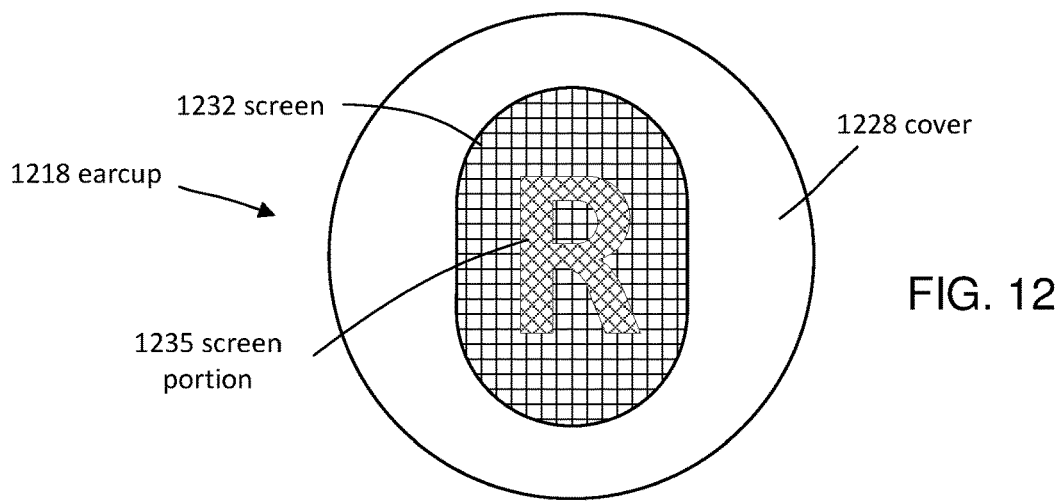

Referring to FIG. 12, in another example embodiment an earcup 1218 includes a cover 1228 and a screen 1232. The cover 1228 can at least partially encompasses a cover support, such as an ear pad. The screen 1232 can include one or more screen portions 1235 that form indicia to provide visual information to a user. For example, earcup 1218 can be configured to be replaceable in a headphone device and the indicia can provide a visual indication of the orientation, which acoustic assembly (i.e., left ear acoustic assembly or a right ear acoustic assembly) of the headphone device corresponds the earcup 1218, and/or the brand of the headphone device corresponding to the earcup 1218. The indicia can include letters, numbers, logos, and/or symbols. In addition, the screen portions 1235 can be configured to having different performance characteristics, such as audio transparency, and/or ventilation, such as by including different knit patterns, and/or materials in the cover 1228.

Figure 13:
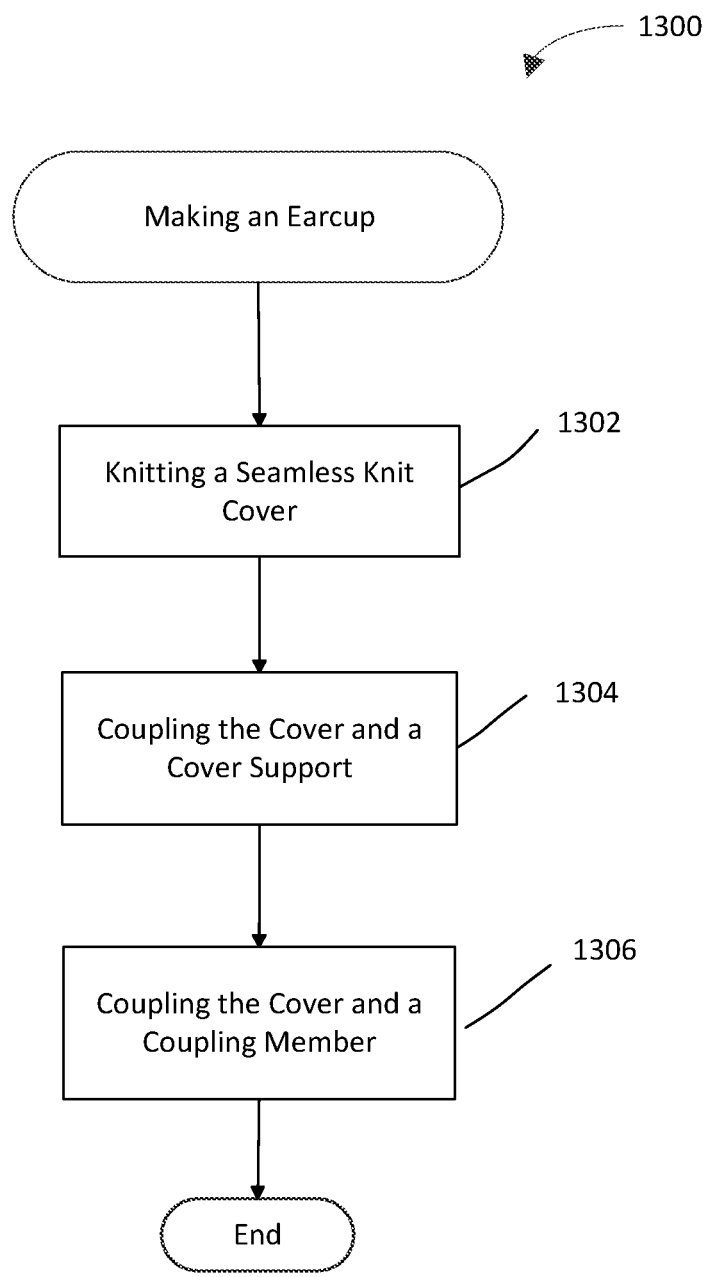
FIG. 13 depicts a flowchart of an example method for making an earcup in accordance with at least one embodiment.

FIG. 13 depicts a flowchart 1300 of an example method of making an earcup in accordance with at least one embodiment. The method of flowchart 1300 can be used to construct the various embodiments of FIGS. 4-9, for example. Further structural and operational embodiments will be apparent to persons skilled in the relevant art(s) based on the discussion regarding flowchart 1300.

As shown in FIG. 13, the method of flowchart 1300 begins at step 1302. In step 1302, a seamless three-dimensional cover is constructed. For example, the seamless three-dimensional cover can be constructed by knitting the cover, such as by using a weft-knitting machine. In at least one embodiment, the seamless three-dimensional cover, e.g., cover 428, is knit. In at least one embodiment, the cover, e.g., cover 428, is formed from a continuous contoured fabric of interlocking yarn, and so that it defines an annular cavity.

At step 1304, the cover is coupled to a cover support. The cover can be coupled to the cover support so that the cover support is disposed in the annular cavity. For example, the cover 428 can be coupled to the cover support 429. In an example, the cover support 429 can be formed as an ear pad that is constructed from a cushion material that is inserted into the annular cavity. The cover can be coupled to the cover support using an adhesive. The adhesive can include thermal adhesive, a pressure adhesive, or a UV cured adhesive. In some embodiments, the cover is ultrasonically welded to the cover support.

At step 1306, the cover is coupled to a coupling member. The coupling member provides an interface between the earcup and other structures included in an acoustic assembly. For example, the cover 428 can be coupled to a coupling member 431. The coupling member 431 can be a ring that includes locking features, such as tapered ribs 433, that engage locking features, such as locking tabs 435, of a housing 424 included in an acoustic assembly 404. The coupling member can be coupled to at least one of an outer portion or an inner portion of the cover using an adhesive. The adhesive can include thermal adhesive, a pressure adhesive, or a UV cured adhesive. In some embodiments, the cover is ultrasonically welded to the coupling member.

In some embodiments, the method further comprises finishing the cover to clean the fabric that forms the cover. For example, a lubricant and/or other debris can be present on the fabric after performing a knitting process. The cover can be cleaned to remove the lubricant and/or other debris so that additional finishing processes can be performed, and/or to improve the coupling between the cover and the cover support and/or coupling member.

In some embodiments, the method further comprises finishing the cover to alter the texture of the cover. For example, finishing the cover can include altering the surface features of a filament, the yarn, or the fabric to provide a different feel to a user. In an example, the surface can be roughened to provide a softer feel.

III. Further Discussion of Some Example Embodiments (A1) A first headphone earcup (e.g., FIG. 4, 418) comprises a cover support (e.g., FIG. 4, 429), a coupling member (e.g., FIG. 4, 431), and a seamless three-dimensional knit cover (e.g., FIG. 4, 428). The cover support forms an earpad. The coupling member is configured to couple the earcup to an acoustic assembly housing (e.g., FIG. 4, 424). The seamless three-dimensional knit cover encloses the ear pad and is coupled to the coupling member. The knit cover defines an annular cavity for the ear pad, and is formed from a continuous contoured fabric of interlocking yarn. The knit cover comprises an outer portion (e.g., FIG. 4, 434), an inner portion (e.g., FIG. 4, 436), and an intermediate portion (e.g., FIG. 4, 438). The inner portion forms a side wall of a sound hole (e.g., FIG. 4, 419) of the earcup. The intermediate portion extends between the outer portion and the inner portion and has an aperture that defines a perimeter of an opening of the sound hole. The intermediate portion has a different stiffness than at least one of the inner portion and the outer portion, and the different stiffness is due to at least one of a different knit pattern and a different fabric material.

(A2) In the headphone earcup of A1, the knit cover further including a screen (e.g., FIG. 4, 432) extending across the sound hole.

(A3) In the headphone earcup of A2, where the screen defines a first acoustic transparency value, and at least one of the outer portion, the inner portion, or the intermediate portion defines a second acoustic transparency value that is different from the first acoustic transparency value.

(A4) In the headphone earcup of A2, where the earcup further comprises a screen support flange (e.g., FIG. 4, 430) extending radially inward from the inner portion, and the screen is coupled to the screen support flange.

(A5) In the headphone earcup of A4, where the screen support flange has a first stiffness, the intermediate portion has a second stiffness, and the first stiffness is greater than the second stiffness.

(A6) In the headphone earcup of A4, where the screen support flange (e.g., FIG. 6, 630) is integrated into the knit cover (e.g., FIG. 6, 628).

(A7) In the headphone earcup of any of A1-A6, where the ear pad is a cushion member comprising a foam.

(A8) In the headphone earcup of any of A1-A7, where the coupling member is a ring and comprises a plurality of tapered ribs (e.g., FIGS. 4 and 5, 433) that are configured to engage a plurality of locking tabs (e.g., FIG. 4, 435) on the acoustic assembly housing.

(A9) In the headphone earcup of any of A1-A8, where the coupling member (e.g., FIG. 8, 831) is a flexible flange extending from the outer portion.

(A10) In the headphone earcup of any of A1-A9, where the yarn comprises at least one of a thermoset material or a thermoplastic material.

(B1) A second headphone earcup (e.g., FIG. 4, 418) comprises a cover support (e.g., FIG. 4, 429), a coupling member (e.g., FIG. 4, 431), and a seamless three-dimensional knit cover (e.g., FIG. 4, 428). The cover support forms an ear pad. The coupling member is configured to couple the earcup to an acoustic assembly housing (e.g., FIG. 4, 424). The seamless three-dimensional knit cover is coupled to the coupling member. The knit cover defines an annular cavity and is coupled to the ear pad such that the cover support is disposed in the cavity. The knit cover is formed from a continuous contoured fabric of interlocking yarn. The knit cover comprises an outer portion (e.g., FIG. 4, 434), an inner portion (e.g., FIG. 4, 436), and an intermediate portion (e.g., FIG. 4, 438). The outer portion is configured to have a first acoustic transparency value. The inner portion forms a side wall of a sound hole (e.g., FIG. 4, 419) and is configured to have a second acoustic transparency value. The intermediate portion is configured to have a third acoustic transparency value. The intermediate portion extends between the outer portion and the inner portion and defines a perimeter of the sound hole. The first acoustic transparency value is different than at least one of the second acoustic transparency value or the third acoustic transparency value.

(B2) In the headphone earcup of B1, where the knit cover further comprises a screen support flange (e.g., FIG. 4, 430) extending radially inward from the inner portion.

(B3) In the headphone earcup of B2, where the knit cover further comprises a screen (e.g., FIG. 4, 432) extending from the screen support flange across the sound hole.

(B4) In the headphone earcup of B2, where the yarn disposed in the screen support flange comprises at least one of a thermoset material or a thermoplastic material.

(B5) In the headphone earcup of B1-B4, where the coupling member is coupled to at least one of the outer portion or the inner portion. The second aspect of the second example headphone earcup can be implemented in combination with the first aspect of the second example headphone earcup, though the example embodiments are not limited in this respect.

(C1) A method of making a headphone earcup comprises knitting a seamless three-dimensional knit cover (e.g., FIG. 13, 1302), coupling a cover support to the knit cover (e.g., FIG. 13, 1304), and coupling a coupling member to the knit cover (e.g., FIG. 13, 1306). The knit cover (e.g., FIG. 4, 428) defines an annular cavity. The knit cover is formed from a continuous contoured fabric of interlocking yarn and comprises an outer portion (e.g., FIG. 4, 434), an inner portion (e.g., FIG. 4, 436), and an intermediate portion (e.g., FIG. 4, 438). The inner portion forms a side wall of a sound hole. The intermediate portion defines an aperture that forms an opening of the sound hole (e.g., FIG. 4, 419) and extending between the outer portion and the inner portion. The cover support (e.g., FIG. 4, 429) is coupled to the knit cover so that the cover support is disposed in the annular cavity, and the cover support forms an ear pad. The coupling member (e.g., FIG. 4, 431) is coupled to at least one of the outer portion or the inner portion.

(C2) In the method of C1, where the seamless three-dimensional knit cover is knit using a weft-knitting machine.

(C3) In the method of C1-C2, where the method further comprises finishing the three-dimensional knit cover to clean the knit cover.

(C4) In the method of C1-C3, where the method further comprises finishing the three-dimensional knit cover to alter the texture of the knit cover.

(C5) In the method of C1-C4, where the coupling member is coupled to at least one of the outer portion or the inner portion using an adhesive.

IV. CONCLUSION

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

What is claimed is:

1. A headphone earcup, comprising:
   a cover support forming an ear pad;
   a coupling member configured to couple the earcup to an acoustic assembly housing; and
   a seamless three-dimensional knit cover enclosing the ear pad and coupled to the coupling member, the knit cover defining an annular cavity for the ear pad, the knit cover formed from a continuous contoured fabric of interlocking yarn and comprising:
   an outer portion;
   an inner portion forming a side wall of a sound hole of the earcup; and
   an intermediate portion extending between the outer portion and the inner portion, and having an aperture that defines a perimeter of an opening of the sound hole, wherein the intermediate portion has a different stiffness than at least one of the inner portion and the outer portion, and wherein the different stiffness is due to at least one of a different knit pattern and a different fabric material.

2. The headphone earcup of claim 1, wherein the knit cover further comprises a screen extending across the sound hole.

3. The headphone earcup of claim 2, wherein the screen defines a first acoustic transparency value, and wherein at least one of the outer portion, the inner portion, or the intermediate portion defines a second acoustic transparency value that is different from the first acoustic transparency value.

4. The headphone earcup of claim 2, further comprising a screen support flange extending radially inward from the inner portion, wherein the screen is coupled to the screen support flange.

5. The headphone earcup of claim 4, wherein the screen support flange has a first stiffness, the intermediate portion has a second stiffness, and the first stiffness is greater than the second stiffness.

6. The headphone earcup of claim 4, wherein the screen support flange is integrated into the knit cover.

7. The headphone earcup of claim 1, wherein the ear pad is a cushion member comprising a foam.

8. The headphone earcup of claim 1, wherein the coupling member is a ring and comprises a plurality of tapered ribs that are configured to engage a plurality of locking tabs on the acoustic assembly housing.

9. The headphone earcup of claim 1, wherein the coupling member is a flexible flange extending from the outer portion.

10. The headphone earcup of claim 1, wherein the yarn comprises at least one of a thermoset material or a thermoplastic material.

11. A headphone earcup, comprising:
a cover support forming an ear pad;
a coupling member configured to couple the earcup to an acoustic assembly housing; and
a seamless three-dimensional knit cover coupled to the coupling member, the knit cover defining an annular cavity and coupled to the ear pad such that the cover support is disposed in the cavity, the knit cover formed from a continuous contoured fabric of interlocking yarn and comprising:
an outer portion configured to have a first acoustic transparency value;
an inner portion forming a side wall of a sound hole and configured to have a second acoustic transparency value; and
an intermediate portion configured to have a third acoustic transparency value, the intermediate portion extending between the outer portion and the inner portion, and defining a perimeter of the sound hole,
wherein the first acoustic transparency value is different than at least one of the second acoustic transparency value or the third acoustic transparency value.

12. The headphone earcup of claim 11, wherein the knit cover further comprises a screen support flange extending radially inward from the inner portion.

13. The headphone earcup of claim 12, wherein the knit cover further comprises a screen extending from the screen support flange across the sound hole.

14. The headphone earcup of claim 12, wherein the yarn disposed in the screen support flange comprises at least one of a thermoset material or a thermoplastic material.

15. The headphone earcup of claim 11, wherein the coupling member is coupled to at least one of the outer portion or the inner portion.

16. A method of making a headphone earcup, comprising:
knitting a seamless three-dimensional knit cover, the knit cover defining an annular cavity, the knit cover formed from a continuous contoured fabric of interlocking yarn and comprising an outer portion, an inner portion forming a side wall of a sound hole, an intermediate portion defining an aperture that forms an opening of the sound hole and extending between the outer portion and the inner portion, the knit cover formed such that at least one of:
the outer portion has a different acoustic transparency than at least one of the inner portion or the intermediate portion; or
the intermediate portion has a different stiffness than at least one of the inner portion or the outer portion, the different stiffness due to at least one of a different knit pattern or a different fabric material;
coupling a cover support to the knit cover so that the cover support is disposed in the annular cavity, wherein the cover support forms an ear pad; and
coupling a coupling member to the knit cover, wherein the coupling member is coupled to at least one of the outer portion or the inner portion.

17. The method of claim 16, wherein the seamless three-dimensional knit cover is knit using a weft-knitting machine.

18. The method of claim 16, further comprising finishing the three-dimensional knit cover by cleaning the knit cover.

19. The method of claim 16, further comprising finishing the three-dimensional knit cover by altering the texture of the knit cover.

20. The method of claim 16, wherein the coupling member is coupled to at least one of the outer portion or the inner portion using an adhesive.

* * * * *